United States Patent
Imam (10) Patent No.: US 8,078,261 B2
(45) Date of Patent: Dec. 13, 2011

(54) LIGHT-GUIDED TRANSLUMINAL CATHETER

(75) Inventor: Farhad B. Imam, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 12/636,975

(22) Filed: Dec. 14, 2009

(65) Prior Publication Data

US 2010/0094126 A1   Apr. 15, 2010

Related U.S. Application Data

(63) Continuation of application No. 11/509,203, filed on Aug. 24, 2006, now abandoned.

(51) Int. Cl.
   *A61B 19/00* (2006.01)
(52) U.S. Cl. .......................................... 600/424
(58) Field of Classification Search ............. 600/424, 600/473, 476; 604/510; 128/899
   See application file for complete search history.

(56) References Cited

U.S. PATENT DOCUMENTS

| | | |
|---|---|---|
| 3,941,119 A | 3/1976 | Corrales |
| 4,096,862 A | 6/1978 | DeLuca |
| 4,248,214 A | 2/1981 | Hannah |
| 4,444,185 A | 4/1984 | Shugar |
| 4,567,882 A * | 2/1986 | Heller ........................ 600/249 |
| 4,729,068 A | 3/1988 | Ohe |
| 4,747,833 A | 5/1988 | Kousai |
| 4,771,782 A | 9/1988 | Millar |
| 4,772,093 A | 9/1988 | Abele et al. |
| 4,782,819 A | 11/1988 | Adair |
| 4,850,358 A | 7/1989 | Millar |
| 4,875,897 A | 10/1989 | Lee |
| 4,898,175 A | 2/1990 | Noguchi |
| 4,909,796 A | 3/1990 | Hagio |
| 4,934,340 A | 6/1990 | Ebling |
| 4,945,895 A | 8/1990 | Takai et al. |
| 4,966,148 A | 10/1990 | Millar |
| 5,005,180 A | 4/1991 | Edelman et al. |
| 5,005,573 A | 4/1991 | Buchanan |
| 5,005,592 A | 4/1991 | Cartmell |
| 5,007,408 A | 4/1991 | Ieoka |
| 5,019,040 A | 5/1991 | Itaoka et al. |
| 5,054,500 A | 10/1991 | Littleford |
| 5,125,404 A | 6/1992 | Kittrell et al. |
| 5,131,380 A | 7/1992 | Heller et al. |

(Continued)

FOREIGN PATENT DOCUMENTS

EP   0214712   3/1987

(Continued)

OTHER PUBLICATIONS

International Search Report for PCT/US06/34887.

(Continued)

*Primary Examiner* — Tse Chen
*Assistant Examiner* — Elmer Chao
(74) *Attorney, Agent, or Firm* — Altera Law Group, LLC (57) ABSTRACT

Generally, the present invention is directed to a light-guided catheter for direct visualization of placement through the skin. An embodiment of the invention includes a method for transcutaneous viewing and guiding of intracorporeal catheters into a body that comprises inserting a catheter into the body having at least one lumen and internally illuminating the catheter with light capable of propagating through the blood and tissue to an external viewer outside of the body.

5 Claims, 5 Drawing Sheets

U.S. PATENT DOCUMENTS

| | | |
|---|---|---|
| 5,142,155 A | 8/1992 | Mauze |
| 5,178,616 A | 1/1993 | Uemiya et al. |
| 5,179,961 A | 1/1993 | Littleford |
| 5,196,004 A | 3/1993 | Sinofsky |
| 5,197,470 A | 3/1993 | Helfer et al. |
| 5,217,456 A | 6/1993 | Narciso, Jr. |
| 5,263,928 A | 11/1993 | Trauthen et al. |
| 5,268,570 A | 12/1993 | Kim |
| 5,290,275 A | 3/1994 | Kittrell et al. |
| 5,306,244 A | 4/1994 | Shiber |
| 5,370,640 A | 12/1994 | Kolff |
| 5,415,654 A | 5/1995 | Daikuzono |
| 5,423,311 A | 6/1995 | Snoke et al. |
| 5,423,321 A | 6/1995 | Fontenot |
| 5,448,582 A | 9/1995 | Lawandy |
| 5,453,086 A | 9/1995 | Weber |
| 5,456,680 A | 10/1995 | Taylor et al. |
| 5,496,305 A | 3/1996 | Kittrell et al. |
| 5,514,128 A | 5/1996 | Hillsman et al. |
| 5,517,997 A | 5/1996 | Fontenot |
| 5,522,389 A | 6/1996 | Fischer et al. |
| 5,540,691 A | 7/1996 | Elstrom et al. |
| 5,626,134 A | 5/1997 | Zuckerman |
| 5,643,251 A | 7/1997 | Hillsman et al. |
| 5,665,052 A | 9/1997 | Bullard |
| 5,728,079 A | 3/1998 | Weber |
| 5,728,092 A | 3/1998 | Doiron et al. |
| 5,733,277 A | 3/1998 | Pallarito |
| 5,803,083 A | 9/1998 | Buck |
| 5,879,306 A | 3/1999 | Fontenot et al. |
| 5,902,247 A | 5/1999 | Coe |
| 5,906,579 A | 5/1999 | Vander Salm et al. |
| 5,947,958 A | 9/1999 | Woodard et al. |
| 5,951,482 A | 9/1999 | Winston |
| 5,964,757 A | 10/1999 | Ponzi |
| 5,993,382 A | 11/1999 | Pruitt |
| 5,995,208 A | 11/1999 | Sarge et al. |
| 6,013,072 A | 1/2000 | Winston |
| 6,022,334 A | 2/2000 | Edwards |
| 6,048,349 A | 4/2000 | Winston et al. |
| 6,061,587 A | 5/2000 | Kucharczyk et al. |
| 6,063,093 A | 5/2000 | Winston et al. |
| 6,081,741 A | 6/2000 | Hollis |
| 6,095,990 A | 8/2000 | Parodi |
| 6,113,588 A | 9/2000 | Duhaylongsod et al. |
| 6,134,003 A | 10/2000 | Tearney et al. |
| 6,146,409 A | 11/2000 | Overholt et al. |
| 6,159,203 A | 12/2000 | Sinofsky |
| 6,230,046 B1 | 5/2001 | Crane et al. |
| 6,236,879 B1 | 5/2001 | Konings |
| 6,246,901 B1 | 6/2001 | Benaron |
| 6,306,097 B1 | 10/2001 | Park |
| 6,332,089 B1 | 12/2001 | Acker et al. |
| 6,364,874 B1 | 4/2002 | Bays |
| 6,366,726 B1 | 4/2002 | Wach et al. |
| 6,402,719 B1 | 6/2002 | Ponzi |
| 6,419,653 B2 | 7/2002 | Edwards |
| 6,445,943 B1 | 9/2002 | Ferre et al. |
| 6,463,313 B1 | 10/2002 | Winston et al. |
| 6,475,226 B1 | 11/2002 | Belef et al. |
| 6,519,485 B2 | 2/2003 | Wiesmann et al. |
| 6,572,609 B1 | 6/2003 | Farr et al. |
| 6,610,054 B1 | 8/2003 | Edwards |
| 6,659,957 B1 | 12/2003 | Vardi |
| 6,685,666 B1 * | 2/2004 | Fontenot .......................... 604/27 |
| 6,701,176 B1 | 3/2004 | Halperin |
| 6,704,590 B2 | 3/2004 | Haldeman |
| 6,811,544 B2 | 11/2004 | Schaer |
| 6,814,712 B1 | 11/2004 | Edwards |
| 6,852,091 B2 | 2/2005 | Edwards |
| 6,852,109 B2 | 2/2005 | Winston et al. |
| 6,887,229 B1 | 5/2005 | Kurth |
| 6,902,545 B2 | 6/2005 | Bertolero et al. |
| 6,911,017 B2 | 6/2005 | Lee |
| 6,915,154 B1 | 7/2005 | Docherty |
| 2002/0013616 A1 | 1/2002 | Carter et al. |
| 2002/0038120 A1 | 3/2002 | Duhaylongsod et al. |
| 2002/0052597 A1 | 5/2002 | Duhaylongsod et al. |
| 2002/0052621 A1 | 5/2002 | Fried et al. |
| 2002/0115922 A1 | 8/2002 | Waner et al. |
| 2002/0123696 A1 | 9/2002 | Kokate et al. |
| 2002/0127144 A1 | 9/2002 | Mehta |
| 2002/0161290 A1 | 10/2002 | Chance |
| 2003/0092995 A1 | 5/2003 | Thompson |
| 2003/0114732 A1 | 6/2003 | Weblet et al. |
| 2003/0130575 A1 | 7/2003 | Desai |
| 2003/0187360 A1 | 10/2003 | Waner et al. |
| 2003/0191379 A1 | 10/2003 | Benaron et al. |
| 2003/0191398 A1 | 10/2003 | Motz et al. |
| 2004/0019280 A1 | 1/2004 | Waner et al. |
| 2004/0064021 A1 | 4/2004 | Pfeiffer |
| 2004/0064022 A1 | 4/2004 | Korn |
| 2004/0068178 A1 | 4/2004 | Govari |
| 2004/0073120 A1 | 4/2004 | Motz et al. |
| 2004/0092913 A1 | 5/2004 | Hennings et al. |
| 2004/0093044 A1 | 5/2004 | Rychnovsky et al. |
| 2004/0236231 A1 | 11/2004 | Knighton et al. |
| 2005/0070788 A1 | 3/2005 | Wilson et al. |
| 2005/0165462 A1 | 7/2005 | Bays et al. |
| 2005/0240147 A1 | 10/2005 | Makower et al. |
| 2006/0004317 A1 | 1/2006 | Mauge et al. |
| 2006/0009785 A1 | 1/2006 | Maitland et al. |
| 2006/0036164 A1 * | 2/2006 | Wilson et al. .................. 600/424 |
| 2006/0203508 A1 | 9/2006 | Lee |
| 2007/0073160 A1 | 3/2007 | Imam |
| 2007/0248307 A1 | 10/2007 | Page et al. |
| 2008/0033519 A1 | 2/2008 | Burwell et al. |
| 2008/0194973 A1 * | 8/2008 | Imam ........................... 600/478 |

FOREIGN PATENT DOCUMENTS

| | | |
|---|---|---|
| EP | 1527748 | 5/2005 |
| WO | WO 02/103409 | 12/2002 |

OTHER PUBLICATIONS

International Search Report for PCT/US09/37927.

* cited by examiner

LIGHT-GUIDED TRANSLUMINAL CATHETER

This application is a continuation of application Ser. No. 11/509,203, filed 24 Aug. 2006 now abandoned. The application is incorporated herein by reference.

FIELD OF THE INVENTION

The present invention is directed generally to medical devices and more particularly to a light-guided catheter with inside-out transcutaneous illumination and visualization of placement through the skin including a method to locate non-visible blood vessels for catheterization.

BACKGROUND

Generally, to insert a catheter into a blood vessel, the vessel is initially identified via aspiration by a syringe with an attached hollow needle by a technique commonly referred to as the Seldinger technique. When blood is drawn into the syringe this indicates that the vessel has been found. The syringe is then disengaged from the needle and the needle lumen is occluded to prevent a possible air embolism and/or to prevent excessive bleeding. Thereafter, confirmation of needle placement in the vein or artery can be assured by haemodynamic monitoring or checking for pulsatile blood flow. Then, a thin guide wire is introduced, typically through the syringe needle or other introducer device, into the interior of the blood vessel. The needle/introducer device is then withdrawn leaving the guide wire within the vessel, wherein the guide wire projects outwardly beyond the surface of the skin.

At this point, several options are available to a physician for catheter placement. The simplest is to pass the catheter directly into the blood vessel directly over the guide wire. The guide wire is then withdrawn, leaving the catheter in position within the vessel. Correct catheter tip placement may then be verified by x-ray procedures. However, this technique is only possible in cases where the catheter is of a relatively small diameter and not significantly larger than the guide wire. If the catheter to be inserted is significantly larger than the guide wire, a dilator device may be first passed over the guide wire to enlarge the insertion hole. The catheter is then introduced over the dilator/guide wire, and the guide wire and dilator are withdrawn.

The technique may be rather routine and straightforward in cases where the patient's blood vessel is near the surface of the skin and is directly visible. However, there are patients (especially the elderly and newborns) wherein their blood vessels are not easily visible and the initial needle puncture may default to a hunt-and peck routine to find the elusive vessel. Even more, once the elusive vessel is found, the insertion of the catheter is usually a blind procedure with verification of correct catheter tip placement only confirmed after the fact by radiographic methods.

Given this, there is a need for a technique to visualize and/or identify the relative location of non-visible blood vessels for initial catheter entry and subsequent real-time visualization while guiding the catheter for correct tip placement.

SUMMARY OF THE INVENTION

Generally, the present invention is directed to medical devices and more particularly to a light-guided catheter with inside-out transcutaneous illumination and visualization of placement through the skin for the purpose of allowing real-time visual guidance, including a method to locate non-visible blood vessels for catheterization.

One particular embodiment of the invention is directed to a method for transcutaneous viewing and guiding of intracorporeal catheters into a body that comprises inserting a catheter into the body having at least one lumen and internally illuminating the catheter with light capable of propagating through the blood and tissue to an external viewer outside of the body.

Another embodiment of the invention is directed to a method for transcutaneous viewing and guiding of intracorporeal catheters into a body that comprises inserting a catheter into the body having at least one lumen and inserting into the lumen a source of illumination capable of propagating through the blood and tissue to an external viewer outside of the body.

Another embodiment of the invention is directed to a method for transcutaneous viewing and guiding of intracorporeal/intraarterial catheters wherein the internally illuminated catheter emits light of a first color and further includes the step of inserting into the catheter lumen a second source of illumination of a second color different from the first color, both of the colors being capable of propagating through blood and tissue to an external viewer outside of the body, whereby the location of each illumination source can be discerned from outside the body.

Another embodiment of the invention is directed to a method for transcutaneous viewing and guiding of intracorporeal/catheters wherein the internally illuminated catheter is made of a material opaque to visible light and the light emitting device extends beyond the distal end of the catheter.

Another embodiment of the invention is directed to a method of locating non-visible intracorporeal/blood vessels for catheterization comprising illuminating candidate locations with light capable of inducing fluorescence from blood constituents and detecting fluorescent response from the blood constituents thereby selecting the potential site for catheterization based upon detection of a predetermined fluorescent signal.

Another embodiment of the invention is directed to a transcutaneously viewable catheter comprising a tubular member having an insertable end and a first channel along the length of the catheter. The catheter has a removable illumination source in said channel having at least an illuminated end, the source being configured to be extendible through said channel and beyond said end so that when the source is inserted into the channel, the illumination is visible outside the body, and the end thereof can be visually located.

Another embodiment of the invention is directed to a transcutaneously viewable catheter wherein the tubular member is substantially opaque to light from the illumination source; so that when the removable source is extended beyond the end of the member, the illumination is visible outside the body.

Another embodiment of the invention is directed to a transcutaneously viewable catheter wherein the tubular member is partially transparent to light emitted by the illumination source; so that when the illumination source reaches the end of tubular member, an observer can detect the difference in level or color of light transmission as the illumination source exits the tubular member.

Another embodiment of the invention is directed to a transcutaneously viewable catheter wherein the illumination source is leaky and emits light along at least a portion of its length, whether discrete or continuous.

Another embodiment of the invention is directed to a transcutaneously viewable catheter wherein the illumination source emits more light at its end than elsewhere therealong, so that it is possible to easily discern its path and end from outside the body.

Another embodiment of the invention is directed to an apparatus for locating substantially non-visible intracorporeal/blood vessels for catheterization comprising a tubular member having an insertable end and a channel along the length thereof. The apparatus has a removable illumination source insertable in the channel having an illuminated end configured to be extendible through the channel. The illumination source is capable of emitting light of predetermined optical wavelengths to excite fluorescence from blood constituents including an optical channel to receive fluorescence from blood constituents and an optical detector coupled to the optical channel to measure the fluorescence from the blood constituents. This embodiment could be incorporated into all other embodiments for facilitation of initial vessel identification and placement prior to catheter insertion and final optimization of final tip placement.

Another embodiment of the invention is directed to an apparatus for locating substantially non-visible intracorporeal/blood vessels for catheterization wherein an appropriate illumination source would be used, such as a low-loss fiber optic conductor or light-emitting diode.

Another embodiment of the invention is directed to an apparatus for locating substantially non-visible intracorporeal/blood vessels for catheterization wherein the optical channel simultaneously delivers the illumination energy to excite fluorescence and receives fluorescence from blood constituents.

Another embodiment of the invention is directed to an apparatus for locating substantially non-visible intracorporeal/blood vessels for catheterization wherein the optical components include a separator, such as but not limited to a dichroic mirror, to separate illumination and fluorescence signals prior to the optical detector.

Another embodiment of the invention is directed to a transcutaneously viewable catheter comprising a tubular member having an insertable end and a first channel along the length of the catheter, with a first optic having an end and being formed within the tubular member and running substantially the length thereof. At least a portion of the first optic is leaky and an illumination source is connected to the optic to provide illumination at least along a portion of the length of the catheter with an optimized color of light so that the illumination is visible outside the body.

Another embodiment of the invention is directed to a transcutaneously viewable catheter comprising a tubular member having an insertable end and a channel along the length of the catheter, with a first optic embedded within the tubular member and running substantially the length thereof and a second optic inserted into the catheter channel and running substantially the length thereof. At least a portion of both optics are leaky and separate illumination sources of distinguishable colors or intensities are connected to each optic so that when both are illuminated the location of the end of the second optic can be distinguished from the first optic.

Another embodiment of the invention is directed to a transcutaneously viewable catheter comprising a tubular member having an insertable end and a channel along the length of the catheter, with a first optic embedded within the tubular member and running substantially the length thereof and a second optic inserted into the catheter channel and running substantially the length thereof. At least a portion of both optics are leaky, the second optic being leaky only near its end, and separate illumination sources of distinguishable colors are connected to each optic so that when both are illuminated the location of the end of the second optic can be distinguished from the first optic.

Another embodiment of the invention is directed to a transcutaneously viewable catheter comprising a tubular member having a first and second optic embedded within the tubular member and running along the length of the catheter. At least a portion of both optics are leaky, the second optic being leaky proximate its end, and separate illumination sources of distinguishable colors are connected to each optic so that when both are illuminated the location of the end of the second optic can be distinguished from the first optic.

Another embodiment of the invention is directed to a transcutaneously viewable catheter comprising a tubular member having an insertable end and a first channel along the length of the catheter, with a first optic having an end and being formed within the tubular member and running substantially the length thereof. At least a portion of the first optic is leaky and an illumination source is connected to the optic to provide illumination at least along a portion of the length of the catheter with a predetermined color of light so that the illumination is visible outside the body. The catheter further includes an elongated radio opaque element having an end and being insertable through the first channel, so that the location of the end of the elongated element can be distinguished from the first optic and detected from outside the body.

Another embodiment of the invention is directed to a transcutaneously viewable catheter comprising a tubular member having a first and second optic embedded within the tubular member and running along the length of the catheter. At least a portion of both optics are leaky, the second optic being leaky proximate to its end, and separate illumination sources of distinguishable colors are connected to each optic so that when both are illuminated the location of the end of the second optic can be distinguished from the first optic. The catheter further includes an elongated radio opaque element having an end and being insertable through the first channel. In this manner, the location of the end of the elongated element can be detected either visually via fluorescence using the light-emitting optic, or by radio detection (X-ray fluoroscopy techniques) if the optic has been removed.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

In general, the present invention is directed to medical devices and more particularly to a light-guided catheter for direct visualization of placement through the skin. The catheter may be placed intracorporeal (inside the body) by any of the catheterization techniques known to those skilled in the art, and the invention includes, but is not limited to intravenous, intraarterial, or intraluminal placement of the catheter.

Figure 1:
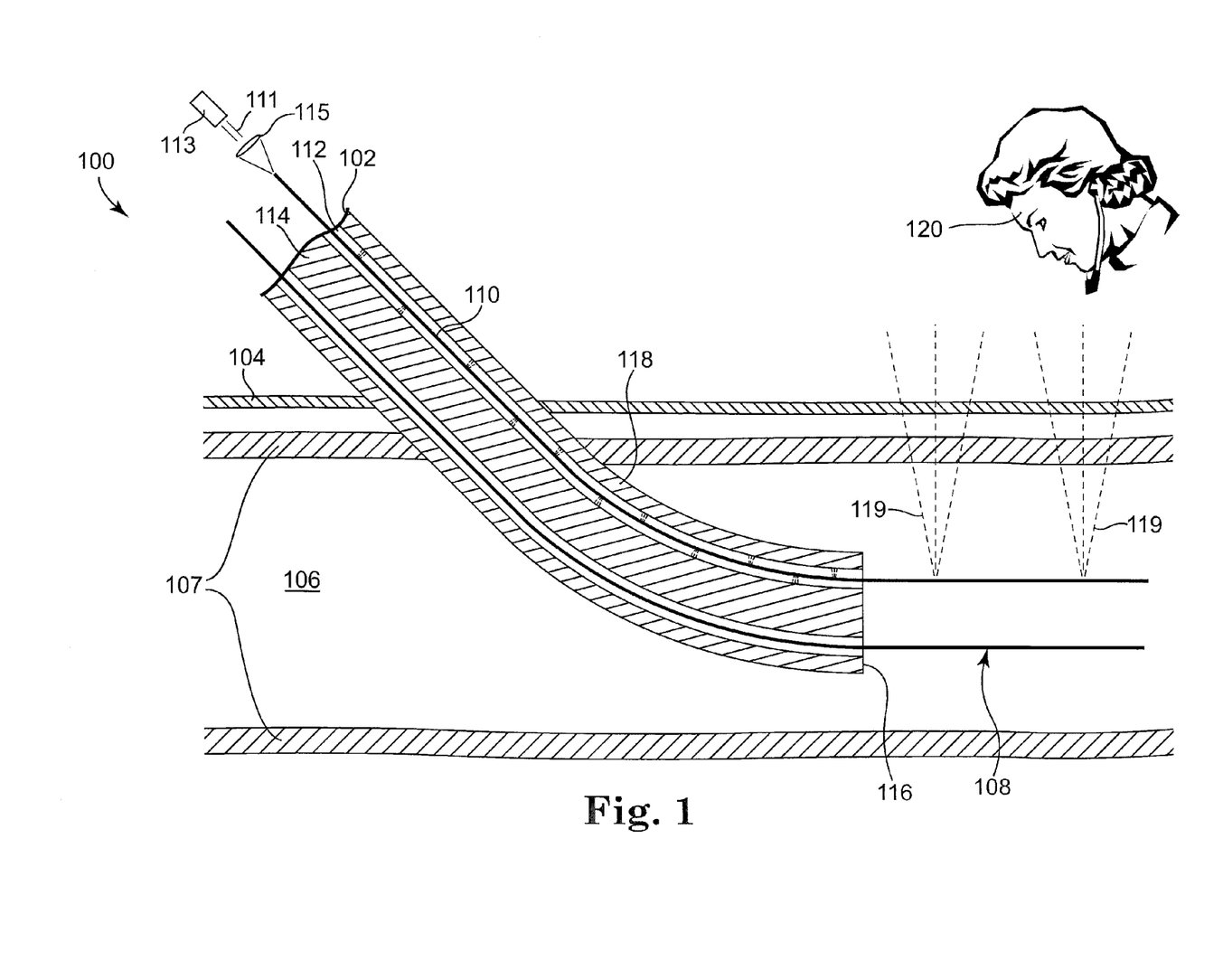
FIG. 1 shows a schematic representation of an optically opaque multi-lumen catheter device inserted into a patient's blood vessel with a fiber optic device inserted into a working channel of the catheter providing inside-out transcutaneous illumination near the distal end of the catheter.

One embodiment of a light-guided transluminal catheter device 100 is depicted schematically in FIG. 1. A multi-lumen catheter 102 is shown having been inserted through the patient's skin 104 and into the blood vessel lumen 106 over the guidewire 108 via the usual insertion techniques (e.g., the Seldinger technique mentioned earlier). A similar catheter without initial guidewire may also be inserted directly through the lumen of the puncturing needle. This is commonly done in the case of peripherally-inserted central catheters (PICC) inserted in an extremity such as the arm or leg and threaded all the way to the heart.

Prior to insertion into the patient's blood vessel lumen 106 through blood vessel wall 107, the surgeon may insert a fiber optical device 110 into an available working channel 112 of the multi-lumen catheter 102. Alternatively, the fiber optic device 110 may be used in lieu of the guidewire following the Seldinger technique described earlier. In this approach, the fiber optic device 110 is inserted through the hypodermic needle and the catheter 102 is introduced into the patient's blood vessel by sliding the catheter over the fiber optic device 110. The fiber optical device 110 may comprise a plurality of "leaky" optical fibers or other light radiating structures which may extend from the exposed end 114 of the catheter 102 to slightly protruding outward from the distal end 116 of the catheter 102 into the patient's blood vessel lumen 106. By leaky, we refer to those optical fibers which radiate or scatter light energy radially outward continuously along at least a portion of the length, i.e. the lateral surface of the fiber. In the preferred embodiment, light emitted would preferably be in the visible light range so that special detection equipment is not required. Illuminating at least a portion of the length of the catheter is desirable, for example, when inserting the catheter it may be highly advantageous to "see" the lateral surface of the catheter when navigating a bend or curve in the patient's blood vessel, which is not uncommon when inserting an intracardiac or "central" catheter from a peripheral location, as in PICC (peripherally inserted central catheter) placement at a distal extremity and threaded toward the heart. In this configuration, the physician may get direct visual confirmation that the catheter is proceeding smoothly "around the bend" without complications. This should be interpreted to mean that a portion of the lateral surface of the catheter, which will be inserted into the body, is capable is emitting illumination. Illumination merely at the tip of the catheter would not be considered to be a portion along the length or lateral surface thereof since the tip is not reasonably considered to be "a length". Likewise, the entire length thereof should be interpreted broadly so as to encompass less than every millimeter of the length, but much of the length which is inserted into the body so that the full pathway can be detected. Light emitting devices 113 may be optically coupled to the optical fibers 110 by means well known in the art of optical communications. For example, light output 111 from the light emitting devices 113 may be coupled into the optical fiber 110 via a focusing lens 115 or other light coupling components. The light emitting devices 113 may be chosen from the list of lasers, light emitting diodes, tungsten-halogen lamps or other suitable light sources with appropriate optical wavelength outputs to be visible by the naked eye or an opto-electronic detector. In the case where opto-electronic detectors are used which may be sensitive to non-visible wavelengths (infrared, ultraviolet, etc.) appropriate alternative light sources and optical fibers may be utilized to generate, guide, and ultimately detect non-visible wavelengths emanating from the fibers.

With respect to the wavelengths of light that have worked best with the catheters, many of them are suitable. The main differences lie in the penetrance of immediate and adjacent tissues, in which the red wavelengths seem to be the most effective (~625-680 nm), but 532 nm (green) also works sufficiently. This general wavelength has the advantage of minimizing the amount of scattering and provides for more precise catheter localization as would the red range at, for example, 5 milliwatts (mw) of power.

Therefore, preferred embodiments might include green (532 nm) and/or red (635 nm) wavelength light sources coupled to the optic, which in preliminary experiments in rabbits and neonatal humans have been able to penetrate >1 cm of tissue and therefore would be visible to the naked eye at depths of up to 1 cm below the skin surface with relatively low light power (<5 mw).

In short, visible light is highly advantageous because no special detection equipment is needed other than perhaps dimming of the ambient room light, which is already routinely practiced in the ICU environment with traditional venous transilluminators to identify vessels for venipuncture and/or arterial puncture.

In the embodiment depicted in FIG. 1, the outer surface 118 of the multi-lumen catheter device 102 may be optically opaque so that only optical radiation 119 emanating from that portion of the optical fiber protruding from the distal end of the catheter 116 may propagate outward through the luminal blood 106/skin 104 regions ultimately to the surgeon's eyes 120 for direct viewing of the in-dwelling location of the catheter tip region 116 (this region being defined as the tip itself and a portion of the catheter extending away from the tip so that a sufficient portion of the catheter can be easily detected. By illuminating only the tip, (essentially a point source) the possibility of an error in detection or reading is increased. This is avoided by illuminating a region adjacent the tip simultaneously. The light emitting devices 113 may be operated continuously, intermittently, or in pulsatile fashion to facilitate visibility through the luminal blood 106/skin 104 regions. Given this, the physician may visually track the location of the distal end region of the catheter 116 as the catheter is maneuvered further upstream in the patient's blood vessel lumen 106 towards the ultimate targeted location. Alternatively, the physician may insert the fiber optical device 110 after the catheter 102 is initially inserted into the patient's blood vessel lumen 106 and guide the catheter 102 by viewing the illuminated distal tip 116 as mentioned above.

Figure 2:
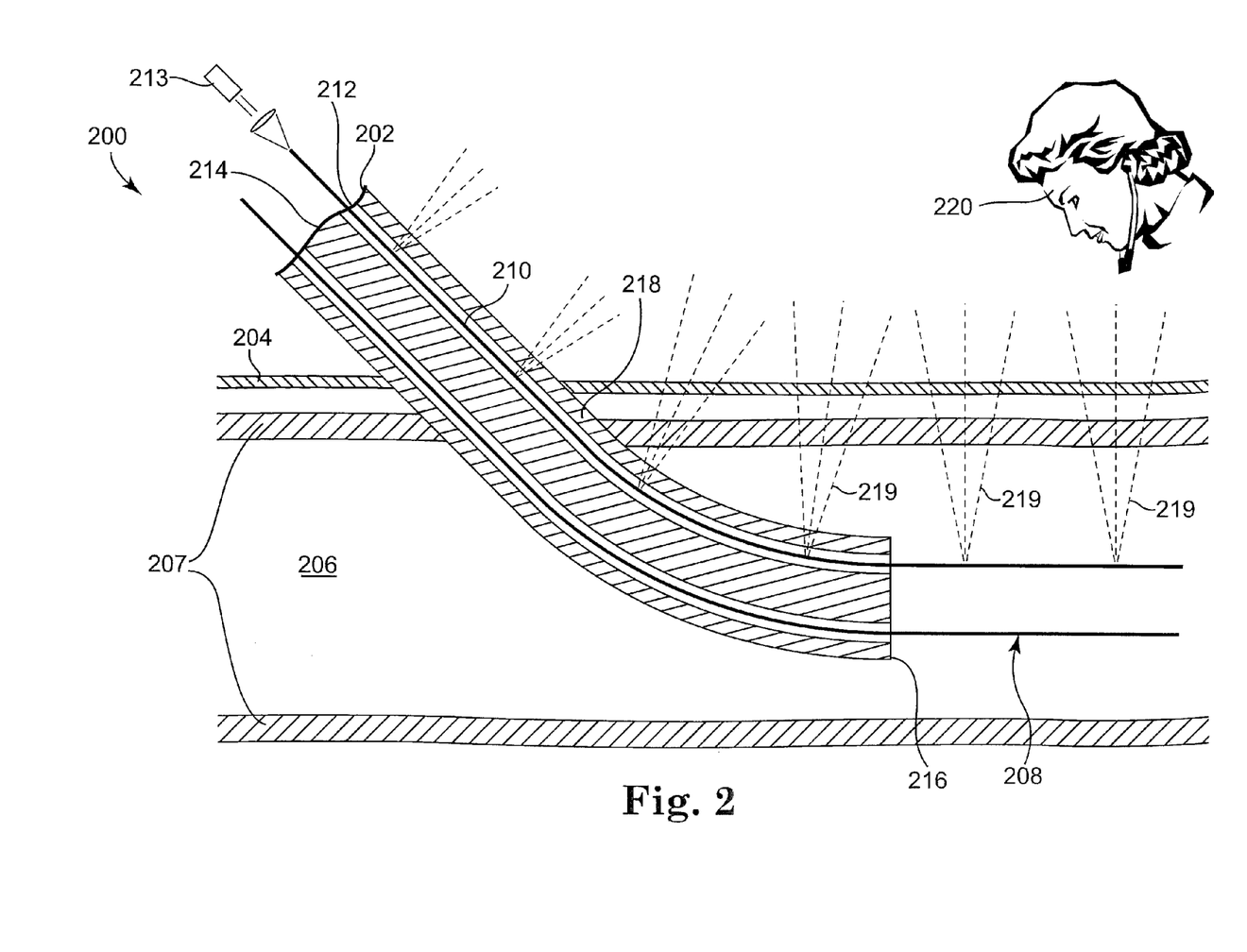
FIG. 2 shows a schematic representation of an optically transparent multi-lumen catheter device inserted into a patient's blood vessel with a fiber optic device inserted into a working channel of the catheter providing inside-out transcutaneous illumination along the length of the catheter.

An alternative embodiment 200 of the present invention is depicted schematically in FIG. 2. A multi-lumen catheter 202 is shown having been inserted through the patient's skin 204 and into the blood vessel 206 over the guidewire 208 via the usual insertion techniques (e.g., the Seldinger technique mentioned earlier).

Prior to insertion into the patient's blood vessel 206, the surgeon may insert a fiber optical device 210 into an available working channel 212 of the multi-lumen catheter 202. The fiber optical device 210 may consist of a plurality of "leaky" optical fibers or other light radiating structures which may extend from the exposed end 214 of the catheter 202 to slightly protruding outward from the distal end 216 of the catheter 202 into the patient's blood vessel 206. By leaky, we refer to those optical fibers which radiate or scatter light energy radially outward continuously along the length of the fiber. Light emitting devices 213 may be optically coupled to the optical fibers 210 by means well known in the art of optical communications. The light emitting devices 213 may be chosen from the list of lasers, light emitting diodes, tungsten-halogen lamps or other suitable light sources with appropriate optical wavelength outputs to be visible by the naked eye.

In the embodiment depicted in FIG. 2, the outer surface 218 of the multi-lumen catheter device 202 may be partially, segmentally, or entirely optically transparent so that optical radiation 219 emanating from the optical fiber may propagate outward along the entire length of the fiber/catheter through the blood 206/skin 204 regions ultimately to the surgeon's eyes 220 for direct viewing of the in-dwelling location of the catheter 202. The outer surface 218 may also modify the intensity, scatter, or wavelength of light passing through it such that the observer or detector would be able to discern the portion of the optic fiber extruded past the catheter tip from the portion lying within it. Given this, the physician may visually track the location of the entire length of the catheter 202 as the catheter is maneuvered further upstream in the patient's blood vessel 206 towards the ultimate targeted location. Alternatively, the physician may insert the fiber optical device 210 after the catheter 202 is initially inserted into the patient's blood vessel 206 and guide the catheter 202 by viewing the illuminated catheter as mentioned above. In an alternative embodiment, the fiber optic device 210 may be inserted into an available working channel 212 of the multi-lumen catheter 202 as before, however, in this case prior to patient insertion the fiber end-face may be withdrawn a sufficient distance back into the distal end 216 of the catheter such that only the lateral surface 218 of the catheter is illuminated. This configuration may eliminate the possibility of the fiber end-face irritating the wall of the patient's blood vessel as the catheter is being inserted, while still illuminating through the lateral surface of a translucent or otherwise non-opaque catheter, the lateral surface 218 of the catheter 202 during insertion and final placement.

In situations where the physician threading the catheter is particularly interested in the location of the catheter tip, the physician may utilize two individual optical fibers 210 to achieve this result. For example, one fiber may be either be pre-loaded into the catheter 202 flush with the distal end 216 of the catheter 202 or the fiber may be embedded in the wall of the catheter 202 terminating at the distal end 216 of the catheter 202. This fiber may be "leaky" along its length and when coupled with a blue LED light source 213, for example, it may illuminate the entire sidewall of the catheter 202 with a blue tint, seen transcutaneously. A second "non-leaky" optical fiber may be inserted into a working lumen of the catheter 202 and may be coupled to a green LED. As the second fiber is inserted into catheter 202 and slightly beyond the distal end 216 of the catheter 202 the transition from blue to green seen transcutaneously may serve as a marker identifying the location of the distal tip 216 of the catheter 202. Of course, different color light sources than the blue/green pair outlined above may be utilized to achieve similar results, wherein in all cases it is preferred that the light sources generate light visible to the naked eye.

An alternative embodiment to locate the distal tip 216 of the catheter 202 incorporates embedding two separate optical fibers in the wall of the catheter 202. Similar to the above embodiment, the first optical fiber may be embedded in the wall of the catheter 202 terminating at the distal end 216 of the catheter 202. The first fiber may be "leaky" along its length and when coupled with a blue LED light source 213, for example, it may illuminate the entire sidewall of the catheter 202 with a blue tint, seen transcutaneously. A second "non-leaky" (i.e., optical energy only radiating from the distal end) fiber may also be imbedded in the wall of the catheter 202 terminating approximately an inch from the distal end 216 of the catheter 202 and may be coupled to a green LED. In this configuration, the transition from a pure blue transcutaneous tint to a blue/green mixture may identify the location of the distal end region 216 of the intracorporeal catheter 202. As before, different choices for the light sources may lead to acceptable alternative color combinations for transcutaneous viewing such as blue/white, green/white, yellow/blue and the like.

Another embodiment of the present invention comprises the combination of a fiber-illuminated catheter used in tandem with a traditional radio-opaque wire used in X-ray fluoroscopy. In this embodiment a single or multiple lumen catheter may have the illuminating and/or radio-opaque fiber either embedded in the wall of the catheter or inserted in an available catheter lumen as before. The radio-opaque wire may be inserted into a vacant catheter lumen or inserted into the same lumen as the illuminating fiber. The illuminating fiber itself may also be radio-opaque (though another embodiment includes a radio-opaque fiber which will both provide propagation of light when connected to a source of illumination, but also be visulizable on radiographs) In this configuration, the physician may multiplex back and forth between the two approaches as necessary. For example, an initial entry into the radial artery (arm) destined for the cardiac region may proceed as follows. Initial entry and threading in the arm may be guided directly by transcutaneous viewing of the fiber-illuminated catheter as outlined before. Upon entry into the chest cavity region, the physician may choose to switch to standard X-ray fluoroscopy when and if the visibility of the fiber-illumination becomes too faint to discern.

Another embodiment of the present invention encompasses a dual-purpose function of the illuminating fiber. In this embodiment the illuminating optical fiber is inserted into an available lumen and illuminates the distal end of the catheter as previously outlined. In addition the fiber may have optically excited chemical sensors attached to the distal end of the fiber. For example, fluorescent dyes sensitive to the dissolved oxygen in blood (sometimes referred to as the partial pressure of oxygen in blood and designated as $pO_2$) are well known and historically have been encapsulated in a polymer membrane attached to the distal end of the sensing fiber. Similarly, additional fluorescent dyes have been demonstrated to respond to the dissolved carbon dioxide in blood ($pCO_2$) as well as the acidity (pH) of blood. The trio above, pO2, pCO2, and blood pH are commonly referred to as a "blood gas" measurement in a hospital setting. A detailed explanation of the mechanism involved for optically sensing "blood gases" by way of fluorescent chemical sensors/dyes attached to the distal end of an optical fiber can be found in U.S. Pat. No. 5,672,515 titled "Simultaneous Dual Excitation Single Emission Fluorescent Sensing Method For pH and $pCO_2$" which is incorporated herein by reference. The additional ability to measure one or more of the "blood gases" while simultaneously viewing the illuminated catheter transcutaneously may allow the physician sufficient information to ascertain whether the catheter has been threaded into arterial or mixed venous blood, given that typical blood gas measurements for venous blood is discernibly different than arterial values.

The above embodiments may also be particularly useful in the placement of peripherally-inserted central catheters (commonly referred to as PICC lines), as well as umbilical artery and vein catheters used in the neonatal intensive care units. PICC lines are commonly introduced into the patient's arm or leg through the lumen of the puncturing needle and threaded all the way to the patient's heart. The PICC lines are subject to being misrouted when inserted and guided (threaded) blindly, and with direct transcutaneous viewing of the catheter while threading, this may be alleviated. The direct transcutaneous viewing of the catheter while threading may be ideal for newborn infants with inherently thin skin, and may also be applicable to a large segment of the adult population, especially the elderly.

Figure 3A:
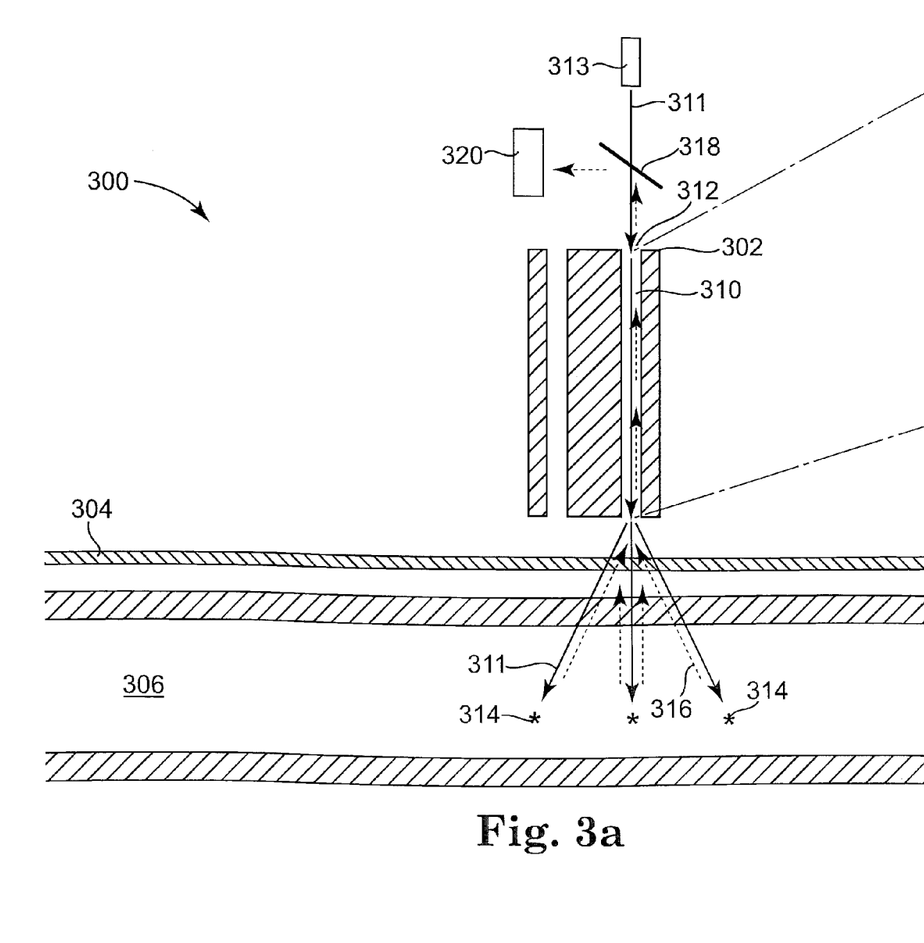
FIG. 3A shows a side-view of a multi-lumen catheter device with a fiber optic inserted into a working channel of the catheter wherein the catheter device is delivering optical radiation to the patient's blood vessel and receiving a fluorescent signal back from chemistry constituents within the patient's blood.
Figure 3B:
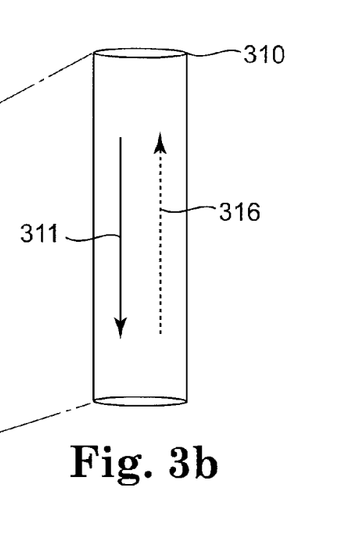
FIG. 3B is an enlargement of the fiber optic device depicted in FIG. 3A, highlighting the counter propagating excitation and fluorescent optical signals traversing the fiber optic device.

An alternative embodiment of the present invention is depicted schematically in FIGS. 3A and 3B. FIG. 3A shows a catheter 300 configured to function as an artery or vein-finder device to optically locate blood vessels which may not be visible directly by the unaided eye. A side view of a multi-lumen catheter 302 is shown in contact with a patient's skin 304 directly over the patient's blood vessel 306. An optical fiber 310 has been inserted into an available working channel 312 of the catheter 302. The optical fiber 310 may be similar to those currently used in optical communications (i.e., "non-leaky" in contrast to the "leaky" fibers depicted in FIGS. 1 and 2) with the ability to waveguide light over long distance with minimal loss out the lateral surface. Light emitting devices 313 may be optically coupled to the optical fibers 310 by means well known in the art of optical communications. The light emitting devices 313 may be chosen from the list of lasers, light emitting diodes, tungsten-halogen lamps or other suitable light sources with appropriate optical wavelength outputs to excite optical fluorescence from chemistries in the underlying blood vessel. In this configuration, the catheter 302 with inserted optics to excite and receive fluorescent signals from chemistries in the underlying blood vessel, may serve as an artery/vein finder to identify the correct location for the initial needle stick (first step in Seldinger technique or in PICC placement) to facilitate the process of eventually placing the catheter in-dwelling. A detailed explanation of the optical technique is described below.

Naturally occurring chemistries in human blood are well known to fluoresce when excited (illuminated) at a particular wavelength corresponding to the absorption band of that chemistry. During the subsequent fluorescence process (which usually occurs on the order of a few nanoseconds after absorbing the illuminating optical energy), the molecule responds by emitting optical energy at a longer wavelength (i.e., lower energy state) than the exciting/illuminating energy. For example, blood constituents bilirubin and carotenoid chromophores are known to fluoresce in the spectral region near 450 nanometers when optically excited (illuminated) at 340 nanometers. Fluorescence form these molecules may be used to locate the position of underlying blood vessels as follows. The light source 313 in FIG. 3A may be chosen to emit optical radiation 311 near 340 nanometers (corresponding to the absorption band of bilirubin for example) which may be coupled into optical fiber 310 which guides the optical radiation 311 to the patient's skin surface 304. The optical radiation 311 may penetrate through the patient's skin 304, traverse the blood vessel wall, enter the patient's blood stream and eventually interact (be absorbed by) a bilirubin molecule 314 present in the patient's blood stream. Thereafter, the bilirubin molecule 314 may re-radiate a fluorescent optical signal 316 (see the expanded view of the fiber 310 shown in FIG. 3B), a portion of which may be coupled back into the optical fiber 310 and guided back toward the light source 313. The returning fluorescent signal 316 may be reflected by partial mirror 318 to optical detector 320 which may have optical filters embedded to only respond to the 340 nanometer signal indicative of bilirubin/blood fluorescence. In this configuration, the optical detector 320 would receive the maximum fluorescent signal back from the bilirubin molecule 314, when the catheter 302/fiber 310 device is directly placed over the underlying blood vessel 306.

Figure 4:
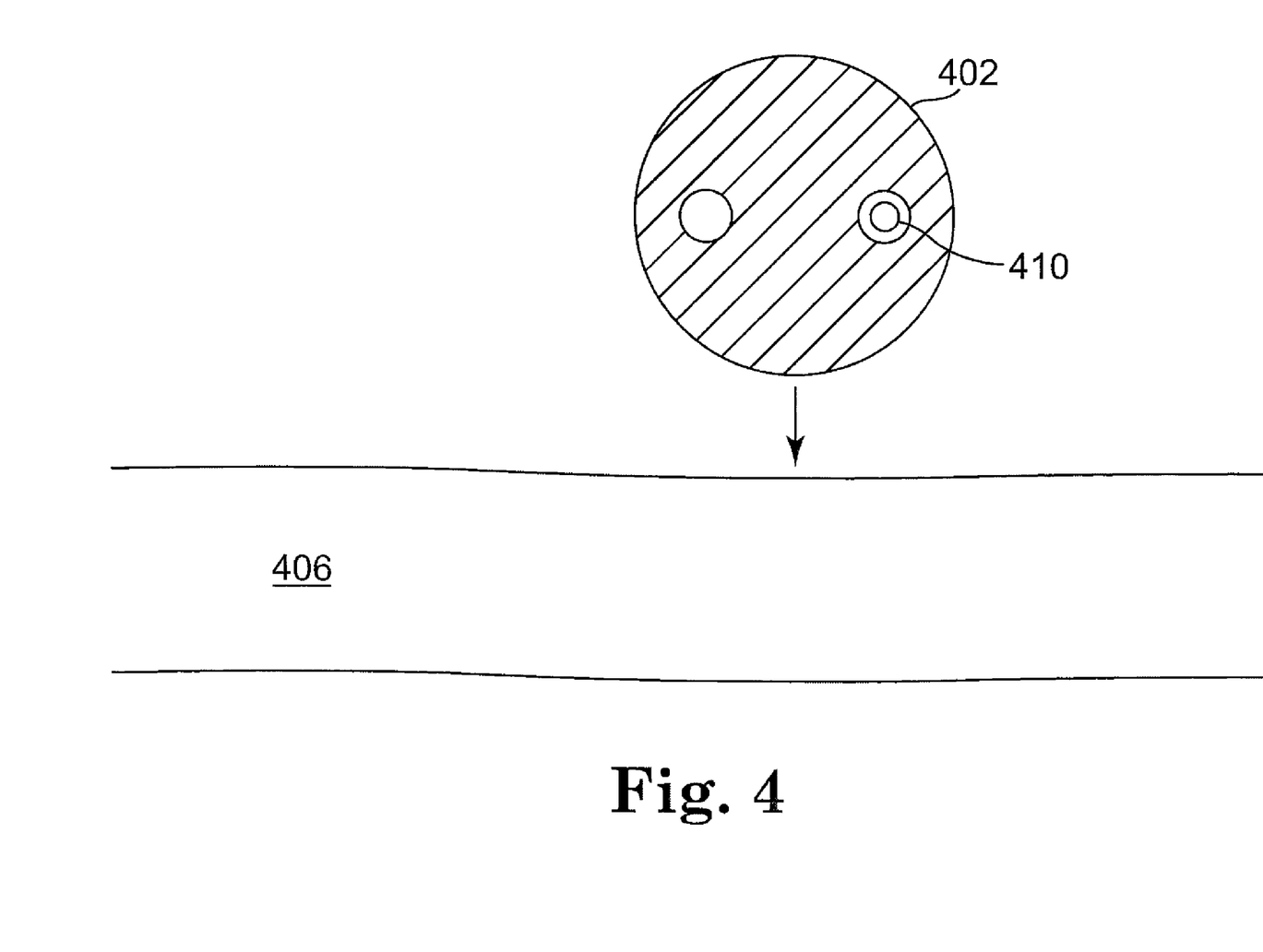
FIG. 4 is a top view (looking down) of the catheter device shown in FIG. 3A showing the catheter device laterally displaced from the underlying patient's blood vessel.
Figure 5:
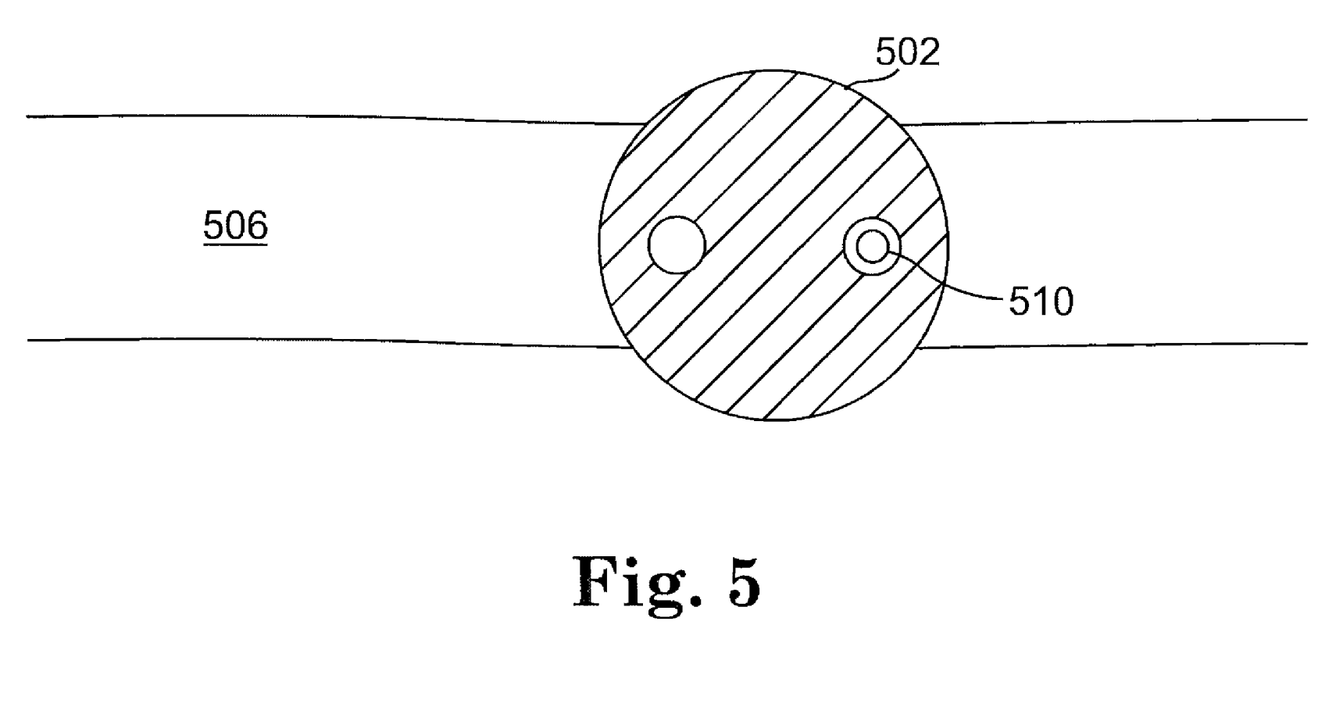
FIG. 5 is a top view (looking down) of the catheter device shown in FIG. 3A showing the catheter device directly centered over the underlying patient's blood vessel.

For example, FIG. 4 shows a top view (looking down on the device depicted in FIG. 3) of the catheter 402 depicting the fiber 410 inserted in the working channel on the right hand side of the catheter 402. The catheter is shown displaced vertically, i.e., off-set from directly over the underlying blood vessel 406, and as such the fluorescent signal 316 (from FIG. 3) capture by the optical fiber 410 will be relatively small. However, when the catheter is translated down directly over the blood vessel (see FIG. 5), the catheter 502 can be manually positioned back-and-forth until a maximum fluorescent signal 316 (FIG. 3) is detected by the optical detector 320 signifying the blood vessel 506 has been located. This process can be repeated at several adjacent points to delineate the course of the vessel subcutaneously and further aid with correct insertion.

As noted above, the present invention is directed generally to medical devices and more particularly to a light-guided catheter with inside-out transcutaneous illumination and visualization of placement through the skin including a method to locate non-visible blood vessels for catheterization.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

I claim:

1. A method for transcutaneous viewing the position of, with the unaided eye and by direct viewing of the in-dwelling location of an intracorporeal catheter, and guiding insertion of said intracorporeal catheter into a body, through body tissue, comprising the steps of:
   a) inserting a catheter into the body, the inserted catheter having a first lumen containing a first leaky optic and a second lumen containing a second leaky optic, the first and second leaky optics running substantially the length of the catheter; and b) illuminating the catheter with a first optical source of illumination and a second optical source of illumination while a human viewer views at least a partial length of the catheter within the body, wherein illuminating the catheter includes said first leaky optic emitting a light of first optical signal propagating through blood and tissue to a human viewer outside of the body, so that the human viewer can detect at least a partial length of the catheter within the body, said first leaky optic emitting a light of first visible color wavelength visible to the naked eye and said second leaky optic emitting a light of a second visible color wavelength visible to the naked eye different from said first color, both of said colors simultaneously propagating through blood and tissue to the human viewer outside of the body viewing the combined light with the unaided eye, and based on the combined light of the first and second wavelengths, distinguishing location and penetration of the catheter by differences in light absorption through the tissue of the two color wavelengths causing externally observed color to vary according to how much of each color wavelength reaches the external viewer.

2. The method of claim 1 further including the step of inserting into said first or second lumen said first or second leaky optic, said first or second leaky optic capable of emitting light capable of propagating through blood and tissue to an external human for direct viewing of the in-dwelling location of the catheter from outside of the body.

3. The method of claim 1 wherein when both optics are illuminated the location of the end of the second optic can be distinguished from the first optic.

4. The method of claim 1 wherein the catheter is made of a material opaque to visible light and:
   a) the first or second leaky optic extends beyond the distal end of the catheter; and/or
   b) the catheter contains emission windows designed at specific regions to allow penetrance of light predominantly at the specific regions.

5. A method for transcutaneous viewing the position of, with the unaided eye by direct viewing of the in-dwelling location of an intracorporeal catheter and guiding insertion of said intracorporeal catheter into a body, comprising the steps of:
   a) inserting a catheter having at least one lumen, into the body; and
   b) illuminating the catheter with a first optical source of illumination and a second optical source of illumination while a human viewer views at least a partial length of the catheter within the body, wherein illuminating the catheter includes a first leaky optic emitting a light of first optical signal propagating through blood and tissue to a human viewer outside of the body, so that the human viewer can detect at least a partial length of the catheter within the body, said first leaky optic emitting a light of first visible color wavelength visible to the naked eye and a second leaky optic emitting a light of a second visible color wavelength visible to the naked eye different from said first color, both of said colors simultaneously propagating through blood and tissue to the human viewer outside of the body viewing the combined light with the unaided eye, and based on the combined light of the first and second wavelengths, distinguishing location and penetration of the catheter by differences in light absorption through the tissue of the two color wavelengths causing externally observed color to vary according to how much of each color wavelength reaches the external viewer; and
   c) providing a plurality of spaced apart discrete leaky points in the first and second leaky optics to allow radial transmission therethrough at said leaky points; whereby the location of the leaky points can be discerned from outside the body with the unaided eye.

* * * * *